United States Patent [19]

Tucknott et al.

[11] Patent Number: 4,633,237
[45] Date of Patent: Dec. 30, 1986

[54] PATIENT BED ALARM SYSTEM

[75] Inventors: Kenneth A. Tucknott, 18701 Stratford Rd., Minnetonka, Minn. 55345; Martin N. Sorenson, Maple Grove, Minn.

[73] Assignee: Kenneth A. Tucknott, Mound, Minn.

[21] Appl. No.: 629,591

[22] Filed: Jul. 11, 1984

[51] Int. Cl.$^4$ .............................................. G08B 23/00
[52] U.S. Cl. .................................. 340/573; 340/575; 340/666
[58] Field of Search ................... 5/508, 424; 340/573, 340/575, 666; 200/DIG. 1, 85 R, 85 A, 86 R; 364/415

[56] References Cited

U.S. PATENT DOCUMENTS

| | | | |
|---|---|---|---|
| 2,644,332 | 7/1953 | Ulrich | 200/85 R |
| 3,961,201 | 6/1976 | Rosenthal | 340/666 X |
| 3,991,746 | 11/1976 | Hanna | 340/573 X |
| 4,020,482 | 4/1977 | Feldl | 340/666 X |
| 4,175,263 | 11/1979 | Triplett et al. | 340/573 |
| 4,228,426 | 10/1980 | Roberts | 340/666 X |
| 4,242,672 | 12/1980 | Gault | 340/573 |

Primary Examiner—James L. Rowland
Assistant Examiner—Brian R. Tumm
Attorney, Agent, or Firm—Lawrence M. Nawrocki

[57] ABSTRACT

Patient bed alarm system (10) is the subject of the present invention. The system (10) includes a plurality of sensors defining interstices (18) of a matrix (16) of such sensors. The matrix (16) is woven into a mat (14) for placement on a bed (12) in which a patient is confined. The presence of the patient's body upon the mat (14) causes various combinations of the sensors to perceive the presence of the patient's body thereon. The particular combinations of sensors sensing the presence of the body is inputted to a first micro computer (20) which discriminates as to the exact location of the patient in view of the exact combination of sensors perceiving the presence of the patient's body. If the combination of sensors actuated indicate an impending vacation of the bed (12) by the patient, an alarm (26, 28) can be actuated by a second micro computer (24) to alert monitoring personnel of the situation.

13 Claims, 3 Drawing Figures

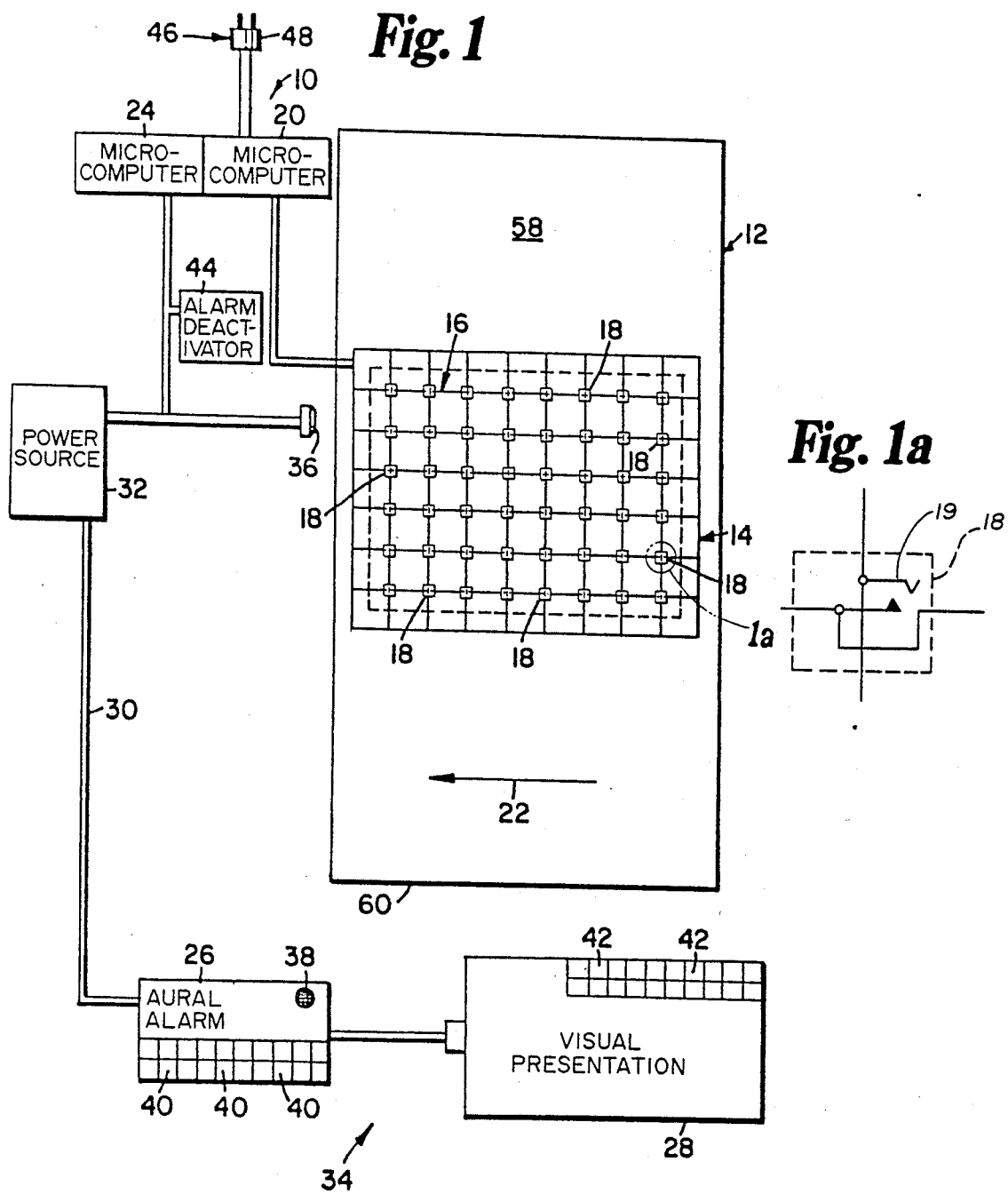
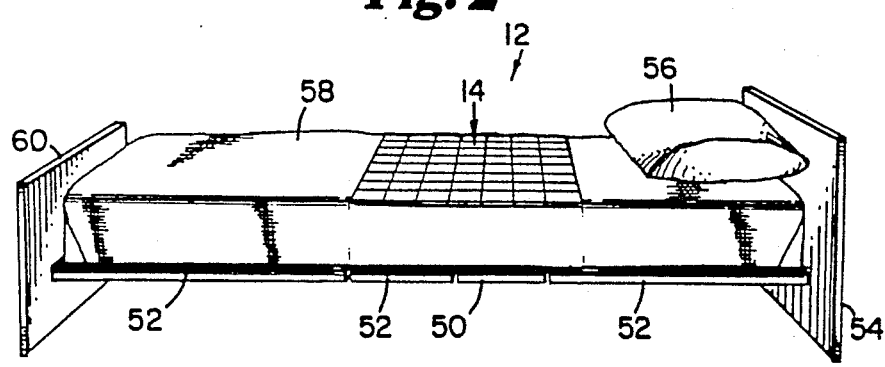

PATIENT BED ALARM SYSTEM

TECHNICAL FIELD

The present invention is related to the field of alarm systems. More specifically, it is directed to the field of systems for detecting and apprising a monitor of the status of a patient confined to a bed in a hospital, nursing home, or other similar institution. In a preferred embodiment, the invention deals with an alarm system which is capable of detecting not only when a patient has vacated a bed, but also when the vacation of the bed by the patient is imminent.

BACKGROUND OF THE INVENTION

Many hospital patients, depending upon their medical condition, are confined to a bed within the institution to which they have been admitted. Confinement may be necessary for any number of reasons. Typically, a doctor might require such a course of action because of the administration of an intravenous solution, because the patient is too weak to be able to negotiate movement to, for example, the bathroom, etc.

Similarly, an admittee to a nursing home might also be confined to bed. Probably the most typical reason for confinement of the patient to bed in an institution of this nature is the weakness of the patient due to old age or infirmity.

Various types of apparatus have been devised to prevent a patient so confined from exiting his or her bed. Probably the most primitive of these apparatus are safety bars secured to the sides of the bed. Such devices, however, have significant restrictions upon the degree of success which can be achieved with their use. Although safety bars might be successful in certain instances in preventing falls from beds, even this is not always true. Because it is often necessary to transfer a patient from the bed into, for example, a wheelchair to transport the patient to another location in the institution, the bars are not continuous along the full length of the bed. If the patient happens to work himself or herself to a location on the bed at which the bars are not present, an inadvertent fall can still occur.

Even more significantly, however, safety bars are totally inadequate to ensure against a volitional vacation of the bed by the patient. If a patient, while lying in the bed, feels sufficiently strong to walk to, for example, the bathroom, he or she will likely be able to move to a discontinuity in the safety bars and exit the bed.

In order to guard against both inadvertent and volitional vacations of a patient from a bed, various types of devices have been constructed. One group of such structures deal with the problem by providing switches, pads, and circuit systems for monitoring at a remote location when a patient has vacated his or her bed. Typical of this type of device are the structures disclosed in U.S. Pat. Nos. Re.28,754 (Cook, et al); 4,172,216 (O'Shea); 4,179,692 (Vance); 4,195,287 (McCoy, et al); 4,228,426 (Roberts); 4,242,672 (Gault); 4,264,904 (McCoy); and 4,295,133 (Vance). The O'Shea patent, along with a number of the other references, teaches a way of monitoring wherein a number of sensing switches are provided. The structures of all of these references, however, merely sense whether a patient is on or off the bed. By the time the sensing has occurred and institutional personnel at a monitor station are alerted to the sensing of the patient being off the bed, the damage may well have already been done, the patient having fallen and injured himself or herself.

While the structures of the above-discussed patents are electrical or electronic in nature, various other devices have been constructed which effect sensing by other means. For example, the structure of U.S. Pat. No. 4,020,482 (Feldl) senses the presence or absence of a patient on a bed by measuring the air pressure in an elongated air inflated flexible bag which is positioned beneath the mattress on which the patient lies. The structure disclosed therein includes an alarm actuation switch which becomes actuated when the pressure in the bag drops below a pre-set actuation pressure. This structure, however, as with the structures of the above-discussed patents, merely detects presence or absence of the patient on the bed.

U.S. Pat. No. 4,245,651 (Frost) discloses an apparatus for detecting body movements on the surface of a bed. It provides an electro-mechanical transducer which has an aural emitter actuated by the compression or expansion of the device in response to movement of the patient, and a microphone for sensing the generated noise. The sensing of the generated noise can, in turn, under appropriate circumstances, initiate the actuation of an alarm. This structure, however, neither senses whether a patient is present or absent upon the bed nor whether he is approaching vacating the bed. Rather, it merely measures the amount of movement of the patient on the bed. In some cases, frequent and exaggerated movement can be indicative of an intent to vacate the bed, but this is not always true.

U.S. Pat. No. 3,961,201 (Rosenthal) illustrates a device similar in structure to the devices of the group of patents initially discussed. That patent teaches the presence of a mechanical switch proximate the edge of a bed which can sense the patient approaching the edge of the frame. When the patient's approaching the edge is sensed, an alarm becomes actuated. The structure of the Rosenthal patent does not, however, provide discrimination as to location of the patient on the bed, and, it would appear, the structure is incapable of being used at all locations about the bed through which the patient might escape.

U.S. Pat. No. 3,836,900 (Mansfield) discloses a mattress for detecting the movement or absence of movement of a patient thereon. The mattress includes resilient resistor material that is varyingly loaded as the patient moves so that changes in its electrical resistance occur giving rise to electrical output signal pulses that are monitored in a detector circuit. The device utilizes a number of layers of the resilient resistor material. The material may be a resilient plastic foam incorporating an electrically conductive material such as graphite, so that movement of one layer relative to a contiguous layer changes the contact resistance. These changes can, in turn, be detected by a suitable electrical circuit to actuate an alarm. As in the case of the structure of the Frost patent, the structure of this patent does not detect either the presence or absence of the patient on the bed or a condition in which the patient is approaching vacating the bed. Rather, it merely detects the volume of movement by the patient while he is on the bed.

U.S. Pat. No. 4,175,263 (Triplett, et al) discloses a structure which includes two sensors for determining the location of a patient on the bed. A first pressure sensing pad detects when the patient is in what the patent defines as a normal position. A second pressure sensor is positioned for sensing the weight of part of a patient's body when the patient moves into a position on the bed in a direction which would indicate an intent to vacate the bed. The structure of Triplett, however, precludes discrimination of location of the patient on the bed. Additionally, it assumes that the patient will attempt to vacate the bed by moving in one certain defined direction. That may or may not always be the case.

The present invention is an improved device which is capable of sensing whether a patient is either on or off the bed. More importantly, however, it can additionally sense where the patient is on the bed, whether the location of the patient is a "safe" location, and when the patient might move to vacate the bed. This is true regardless of the direction in which the patient might move in his attempt to exit from the bed. It is to all of the problems existent in the prior art, therefore, that the current invention is directed.

SUMMARY OF THE INVENTION

The present invention is a device for detecting when a patient confined to a bed in an institution such as a hospital or nursing home has, either inadvertently or volitionally, moved to vacate the bed. The device includes a matrix of sensors which is positionable on the bed to discriminate as to the exact location of the patient. When the person is in a "safe" location, one of a number of defined combinations of sensors will perceive the presence of the body of the patient. When the patient is in a location that, by definition, is one wherein he is approaching exiting from the bed, one of a plurality of defined combinations of the sensors will perceive the presence of the person's body. The device further includes means for determining what combination of sensors perceives the presence of the patient's body and whether that particular combination of sensors indicates that the patient is in a "safe" location on the bed or one in which he is approaching exiting from the bed. An alarm is provided at a station to alert monitoring personnel if the patient is in an unsafe location. Means are provided for actuating the alarm if the combination of sensors perceiving the body of the patient indicates that the patient is in a location indicative of vacating the bed.

In a preferred embodiment, the matrix of sensors includes a plurality of pressure sensitive capacitor switches overlying a mat with respect to which they are held to form a single structure. It has been found that a matrix measuring 6 switches by 8 switches in a mat is optimal for providing a structure to discern the location of the patient. Such a mat can be structured so that it would be dimensioned wherein 8 columns of switches, each column having 6 switches, would extend across the bed generally transversely to the axis of elongation thereof.

The invention described above can be used in combination with a patient bed as typically used in a hospital or nursing home. Such beds typically have a base frame section which defines a horizontal plane which may or may not be able to be elevated or lowered. Regardless of the position of the base frame section, however, it typically defines a horizontal plane. Other frame sections can be used in combination with the base frame section to tilt various portions of the patient's body. For example, a frame section toward the head of the bed from the base frame section might be used to tilt the patient's body upwardly into a sitting or a reclining position for eating or reading, respectively. Frame sections toward the foot of the bed from the base frame section could be used for either elevating or lowering the legs of the patient.

When the present invention is used in combination with such a bed, it would be most typically positioned on the bed with a large portion of the mat being disposed on the base frame section. That portion of the patient's torso most faithfully indicating intended movement would be over the mat, therefore.

In order to be integrable with other hospital and nursing home equipment, the present invention can be interfaced with the standard electrical call system utilized whereby a patient can call a nurse when attention is needed. Typically, such systems include both visual and aural means for alerting a nurse that a patient needs assistance. A first micro computer can be utilized to discriminate what combination of switches has been actuated by the weight of the patient's body. A second micro computer can, along with the first micro computer, be patched into the wiring of the call system so that, when the first micro computer senses a hazardous condition, it will send a signal to the second micro computer which, in turn, will actuate the alarm.

The system can, further, be provided with means for deactivating the alarm, the deactivating means being located only proximate the mat on the bed. As a result, the alarm will remain actuated until the nurse or another monitoring person actually goes to the patient's location to determine the nature of the problem which has created the actuation of the alarm.

Various other features can be incorporated into the present invention. For example, the second micro computer can be constructed so that it generates a wave form signal different from that initiated by a manual actuator in the call system. When the present invention is incorporated into the in-place call system, the alarm signal generated in response to the detection of an unsafe location of a patient in a bed will be different than that actuated by a call by a patient.

The present invention is thus an improved device for sensing not only presence or absence of a patient on a bed, but also movement of a patient which would be indicative of an intent to vacate the bed. More specific features and advantages obtained in view of those features will become apparent with reference to the DETAILED DESCRIPTION OF THE INVENTION, attached claims, and accompanying drawing figures.

BRIEF DESCRIPTION OF THE DRAWINGS

FIG. 1 is a schematic view indicating the overall component relationship of the various parts of the present invention when the invention is incorporated into a standard "call" system in a hospital, nursing home, or other similar institution;

FIG. 1a is a greatly enlarged detail view taken at 1a of FIG. 1; and

FIG. 2 is a perspective view showing a mat in accordance with the present invention as positioned on a bed which might be used in such an institution.

DETAILED DESCRIPTION OF THE INVENTION

Referring now to the drawings wherein like reference numerals denote like elements throughout the several views, FIG. 1 illustrates a patient bed alarm system (10) in accordance with the present invention. The Figure shows a bed (12) on which is positioned a flexible mat (14) which has a matrix (16) of sensors (18) in an overlying relationship. The sensors (18) are positioned at the interstices (19) of the matrix (16), and they can comprise a plurality of pressure sensitive capacitor switches organized into rows and columns. In the embodiment illustrated in FIG. 1, the grid (16) of switches is organized into 8 columns and 6 rows of switches woven into the mat (14). It has been found that a grid (16) having this number of switches is optimum for providing the discrimination necessary in order to obtain the goals of determining the location of a patient on the mat (14), as will be discussed hereinafter. It will be understood, however, that this specific numbering of switches is not essential to the invention.

When a patient confined to the bed (12) with which the mat (14) is used is lying thereon, various combinations of switches will be closed to sense the presence of the patient's body at the particular location. A first micro computer (20) will receive electrical input from the switches in the mat (14), and it will discriminate as to what combination of switches are closed. The first micro computer (20) is programed as desired depending upon recognized "danger locations" of a patient on the bed (12). For example, the micro computer (20) may be programmed to discern and recognize the closing of the four most intermediate columns of switches as one of a first plurality of defined combinations of closed switches indicating a safe condition of the patient. If the patient rolls slightly to the left in a direction indicated by arrow 22, and closes the column of switches the second from the left and, concurrently, opens the column of switches third from the right, the micro computer (20) may still be programmed to recognize this situation as a safe situation or a first defined combination of switch closings indicating a safe condition. As a patient might continue to roll to the left and close, for example, the four left-most or three left most columns of switches, the computer (20) may be programmed to still detect the patient as being at a safe location. When only the two left most columns of switches become closed as a result of the continued movement of the patient to the left, however, the computer (20) may be programmed to recognize this combination of switch closings as one indicating a dangerous situation wherein the patient is approaching vacating the bed.

The micro computer (20) can be programmed to discriminate similar defined combinations of switch closings as the patient moves either to the right, toward the head of the bed, or toward the foot of the bed. The computer (20) can be programmed to discriminate any combination of switch closings as being first defined combinations (or safe combinations) or second defined combinations (or unsafe combinations).

The system (10) further includes a second micro computer (24) which is inputted by the first micro computer (20). When the first micro computer (20) senses a closing of a second defined combination of switches indicative of an unsafe condition, the second micro computer (24) will function to actuate an alarm or alarms (26, 28) in the system to indicate to personnel monitoring the status of a patient or patients that one or more of the patients are approaching an unsafe condition wherein they are approaching vacation of their beds (12). A wave form signal is sent to the alarm or alarms (26, 28) through a transmission line (30). The transmission line (30) as illustrated in FIG. 1 includes a power source (32), and, when the mat and micro computer assembly is used with a typical nurse call system (34) in a hospital, for example, the power source (32) can be that providing power to the call system (34). Similarly, the alarms, (26, 28) both aural and visual, can be those which comprise a part of the in-place nurse call system (34).

A nurse call button would, typically, be provided proximate the bed (12) for the patient to call a nurse if one were needed. Such a call button (36) functions to generate a second wave form signal different from that generated by the second micro computer (24). As a result, the aural presentation made by the audio transducer (38) of the aural alarm means (26) will be different depending upon which wave form signal initiates its actuation. Personnel in the institution monitoring patients can, thereby, quickly ascertain whether a patient is merely calling for an attendant or whether the patient is approaching a situation of vacating his or her bed (12).

When the signal presentation is one indicating the latter situation, the monitoring personnel can quickly check the aural alarm (26) in order to ascertain which of a number of room indicators (40) is lit in order to determine where the patient is attempting to exit his bed (12) or is inadvertently approaching the edge thereof. Similarly, the visual presentation (28) of the alarm can confirm the room number by indicators (42).

The system (10) further includes means (44) for deactivating the alarm (26, 28). In order to ensure that the monitoring personnel attend to the patient, the deactivation means (44) can be positioned in the room of the patient proximate the bed (12) and mat (14) placed thereon.

Rather than relying on the power source (32) of the nurse call system (34) used in the hospital, nursing home, or other similar institution, the mat and micro computer assembly can be provided with its own power source (46). The power source (46) can include a converter (48) which can be plugged into a conventional AC outlet in a wall. The converter (48) can function to transform the alternating current to direct current.

Referring now to FIG. 2, that figure illustrates the most optimum placement of the mat in order to ensure the most effective results therewith. Typically an institutional bed (12) includes a base frame section (50) which may or may not be able to be elevated or lowered. The base frame section (50), however, is typically configured to continuously define a generally horizontally oriented plane regardless of the height at which it is disposed. Additionally, such a bed (12) includes at least one related frame section (52). Figure 2 illustrates one such section between the base frame section (50) and the head board (54) and is shown as having a pillow (56) seated on a portion of a mattress (58) overlying this section (52). Such a section (52) is typically configured for angling upwardly relative to the base frame section (50) in order to position the upper torso and head of the patient in a more upright fashion for reading, eating meals, etc.

Additionally, other frame sections can be positioned toward the foot (60) of the bed (12) from the base frame section (50). Such sections typically are used to elevate or lower the legs and feet of the patient.

In order to maximize efficiency of the present sensing and alarm system (10), the greater portion of the mat (14) would be positioned over the base frame section (50). This is so since the main part of a patient's torso would, when he or she is in a safe position on the bed (12), be positioned over the base frame section (50). The base frame section (50) defines a "safe zone" at which the patient would be unlikely to be moving toward vacating the bed (12).

Numerous characteristics and advantages of the invention for which this application has been submitted have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. Apparatus for discerning the impending, undesired vacation of a bed in a hospital, nursing home, or other institution, by a person confined to the bed, comprising:
   a matrix having a plurality of sensors positionable on the bed in which the person is confined so that, when the person is in a safe location on the bed, certain first defined combinations of said sensors will perceive the presence of the person's anatomy, and, when the person is in a location on the bed wherein he is approaching vacating the bed, certain second defined combinations of said sensors will perceive the presence of the person's anatomy;
   means for discriminating whether a first or second defined combination of sensors is perceiving the presence of the person's anatomy;
   alarm means, for alerting monitoring personnel; and
   means, responsive to said discriminating means, for actuating the alarm means when a second defined combination of sensors is perceiving the presence of the person's anatomy.

2. Apparatus in accordance with claim 1 wherein said matrix having a plurality of sensors comprises a grid of pressure sensitive switches overlying a mat.

3. Apparatus in accordance with claim 2 wherein said pressure sensitive switches comprise capacitor switches.

4. Apparatus in accordance with claim 2 wherein said matrix comprises a grid measuring 6 switches by 8 switches.

5. Apparatus in accordance with claim 4 wherein said mat is configured to be positioned on the bed with its 8 switch dimension extending generally transversely to an axis of elongation of the bed.

6. Apparatus in accordance with claim 5 wherein said 8 switch dimension of said mat extends substantially the full length of the dimension of the bed transverse to said axis of elongation.

7. Apparatus in accordance with claim 1 wherein said alarm means includes means for generating both visual and aural presentations.

8. In combination with an electrical call system in a hospital, nursing home, or other institution, wherein the system includes means for alerting personnel at a monitor station of the call of a bedridden person;
   a flexible mat having a grid of pressure sensitive switches in an overlying relationship thereto and as a part thereof, said mat being positionable on a bed in which a bedridden person is confined so that, when the person is in a safe location on the bed at which there is no impending danger of the person vacating the bed either volitionally or inadvertantly, certain first defined combinations of said switches will be closed by the weight of the person's anatomy, and, when the person is in a location on the bed wherein he is approaching vacating the bed, certain second defined combinations of said switches will be closed by the weight of the person's anatomy;
   first computer means for discriminating whether a first or second defined combination of switches is closed; and
   means for actuating the alerting means when a second defined combination of switches is closed.

9. The combination of claim 8 wherein said actuating means comprises second computer means responsive to said first computer means.

10. The combination of claim 8 wherein the alerting means includes both visual and aural alarm presentations, and further comprising means, isolated at the location of the bed, for deactivating the alarm presentations.

11. In combination with a patient bed having a base frame section defining a plane consistently oriented generally horizontally to accommodate a portion of the torso of a patient thereon and at least one related frame section proximate said base frame section and angleable relative thereto, and with an electrical call system having a manual actuator proximate the bed and an alarm, actuated by a wave form signal initiated by the manual actuator, at a patient monitor station;
    a mat having a multiplicity of pressure sensitive switches organized into rows and columns in an overlying relationship thereto and as a part thereof, said mat being positionable on the bed with the greater portion thereof disposed on the base frame section, wherein, when a patient is in a safe location on the bed at which there is no impending danger of the patient vacating the bed, certain first defined combinations of said switches will be closed by the patient's weight, and, when a patient is in a position in which he is approaching vacating the bed, certain second defined combinations of switches will be closed by the patient's weight;
    a first micro computer for ascertaining whether a first or second defined combination of switches is closed; and
    a second micro computer for actuating the alarm when a second defined combination of switches is closed.

12. The combination of claim 11 wherein said second micro computer, when a second defined combination of switches is closed, initiates a wave form signal different from that initiated by the manual actuator, wherein the presentation of the alarm will be different.

13. The combination of claim 11 further comprising means powering said micro computers and including means for converting alternating current to direct current.

* * * * *